(12) United States Patent
Craft et al.

(10) Patent No.: US 10,507,016 B2
(45) Date of Patent: Dec. 17, 2019

(54) UMBILICAL CATHETERIZATION DEVICE

(71) Applicant: Clinvue LLC, Savage, MD (US)

(72) Inventors: Brandon Wesley Craft, Edgewater, MD (US); Anant Vaidyanathan Subramaniam, Owings Mills, MD (US); Chelsey Nicole Pon, Baltimore, MD (US)

(73) Assignee: Clinvue LLC, Savage, MD (US)

( * ) Notice: Subject to any disclaimer, the term of this patent is extended or adjusted under 35 U.S.C. 154(b) by 0 days.

(21) Appl. No.: 15/186,617

(22) Filed: Jun. 20, 2016

(65) Prior Publication Data

US 2017/0360424 A1 Dec. 21, 2017
US 2019/0167248 A9 Jun. 6, 2019

Related U.S. Application Data

(60) Provisional application No. 62/182,832, filed on Jun. 22, 2015.

(51) Int. Cl.
*A61B 17/02* (2006.01)
*A61B 17/122* (2006.01)

(52) U.S. Cl.
CPC ...... *A61B 17/0293* (2013.01); *A61B 17/0206* (2013.01); *A61B 17/122* (2013.01); *A61B 2017/0287* (2013.01)

(58) Field of Classification Search
CPC .............. A61B 17/122; A61B 17/0206; A61B 17/0293; A61B 2017/0287
USPC .......................................................... 606/120
See application file for complete search history.

(56) References Cited

U.S. PATENT DOCUMENTS

| | | | | |
|---|---|---|---|---|
| 5,234,447 | A * | 8/1993 | Kaster ................... | A61B 17/11 606/151 |
| 7,585,306 | B2 * | 9/2009 | Abbott .................. | A61B 17/11 606/153 |
| 2006/0052670 | A1 * | 3/2006 | Stearns ................ | A61B 1/0056 600/216 |
| 2011/0295291 | A1 * | 12/2011 | Trivisani .............. | A61B 17/122 606/158 |
| 2012/0035630 | A1 * | 2/2012 | Roorda ................ | A61B 17/064 606/155 |

* cited by examiner

*Primary Examiner* — Lynnsy M Summitt
*Assistant Examiner* — Tara Rose E Carter
(74) *Attorney, Agent, or Firm* — Tanner IP, PLLC

(57) ABSTRACT

An umbilical catheterization device that allows a physician to prepare an umbilical cord and apply appropriate retraction to widen vessels to introduce a catheter. The device comprises a base and a plurality of arms. The arms may include retraction devices or may be compatible with independent retraction devices, including but not limited to sutures. The retraction devices are attached to the umbilical cord, and used to provide retraction.

19 Claims, 18 Drawing Sheets

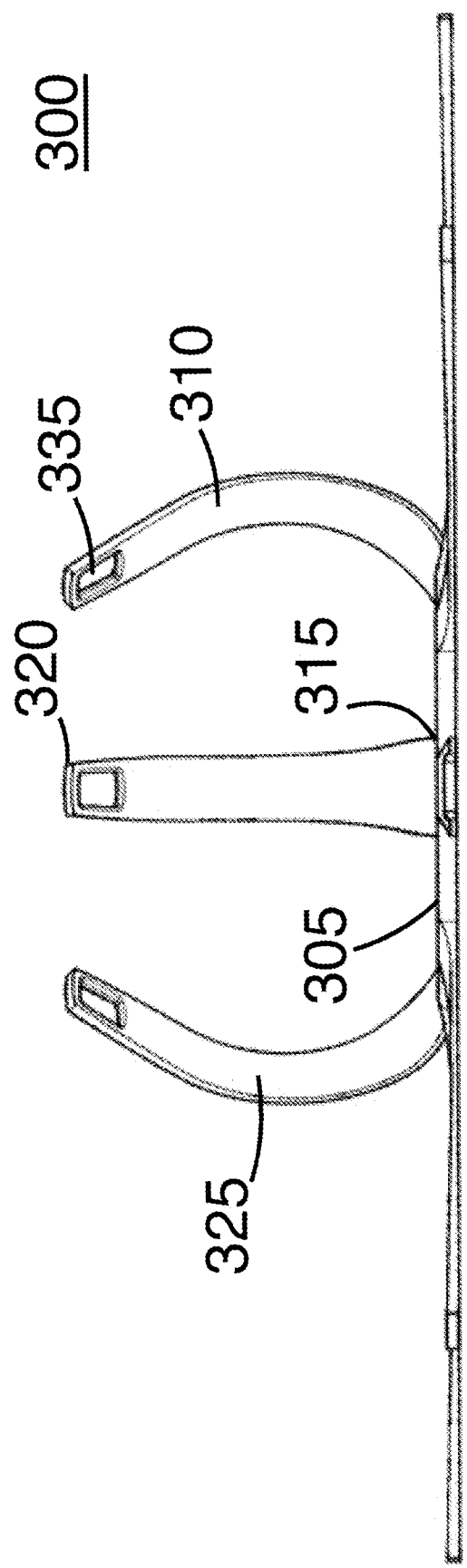

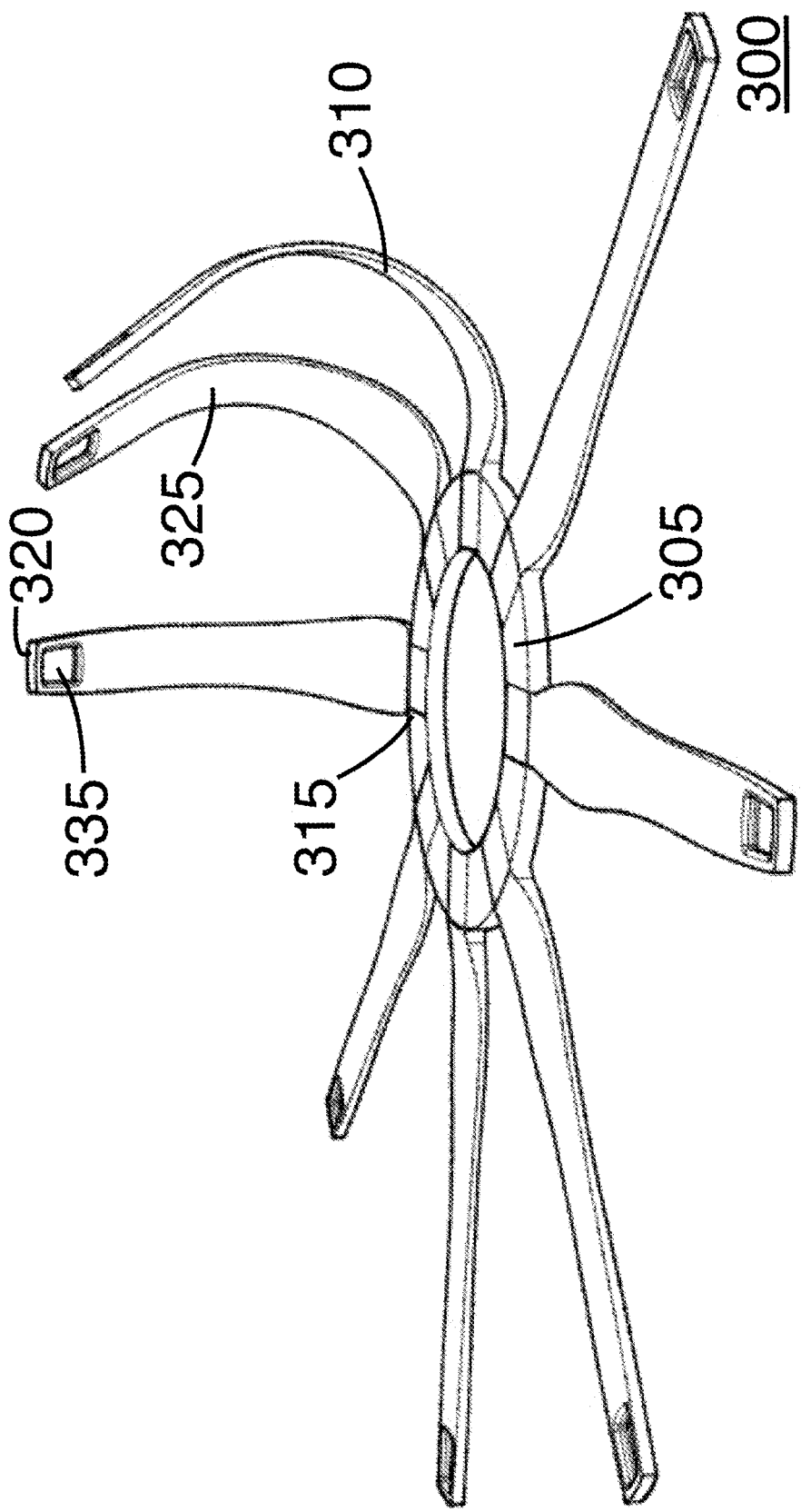

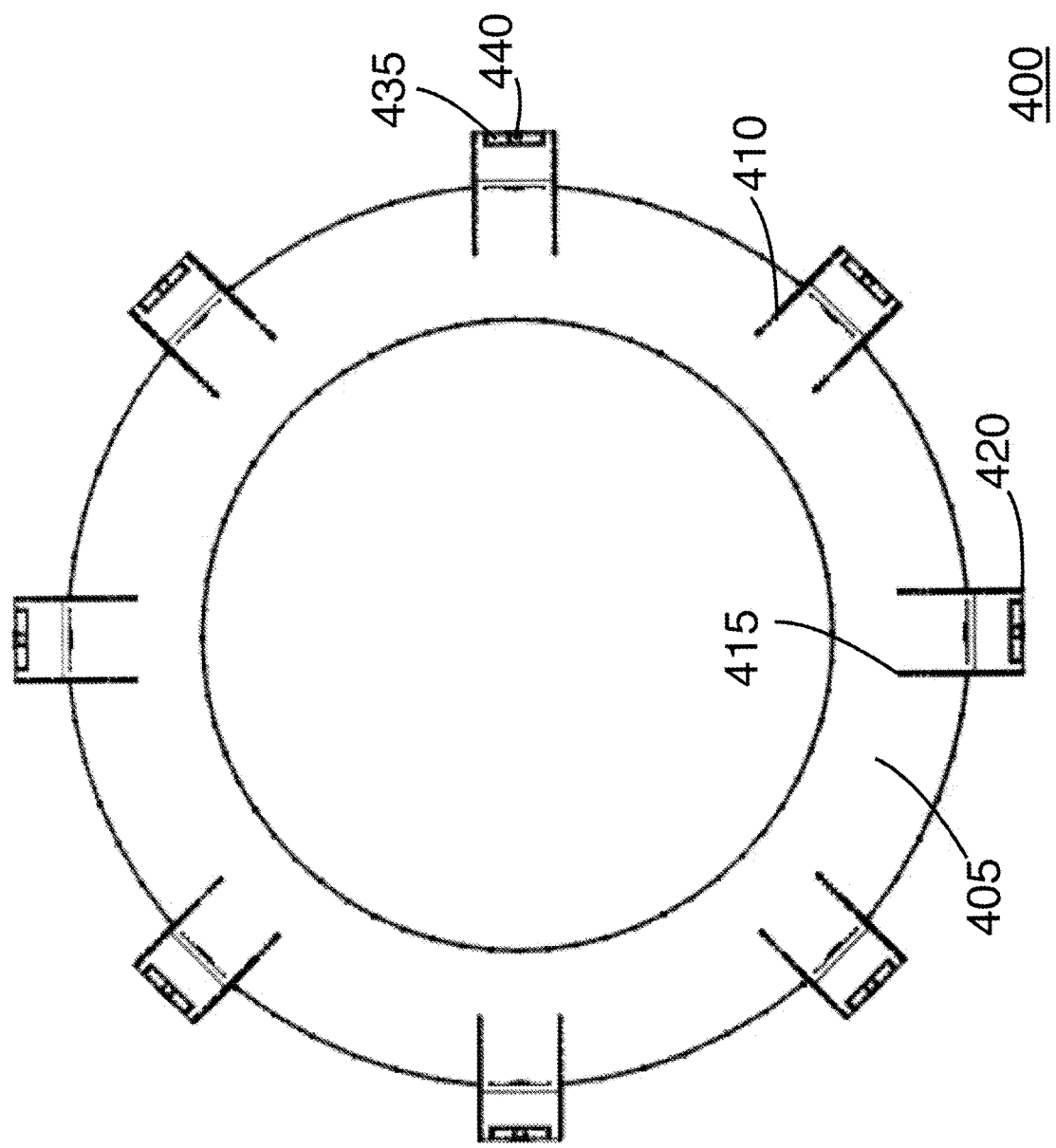

UMBILICAL CATHETERIZATION DEVICE

RELATED APPLICATIONS

This application claims priority under 35 U.S.C. 119(e) to U.S. Provisional Application 62/182,832, filed on Jun. 22, 2015.

BACKGROUND

1. Technical Field

Umbilical catheterization is often performed as a life-sustaining measure in neonates that require resuscitation or monitoring (John P Magnan. 2014. *Umbilical Vein Catheterization. Medscape Reference*. Accessed on 8 Jan. 2015). Catheterization can be performed through either of the two arteries or the vein. Umbilical venous catheterization is most commonly performed for resuscitation and central venous measurement, while arterial catheterization is performed for arterial blood-gas measurements and intravascular delivery of medications (Taylor L Sawyer. 2013. *Umbilical Artery Catheterization. Medscape Reference*. Accessed on 8 Jan. 2015). An estimated 120,000 patients receive umbilical catheterizations each year at neonatal intensive care units (NICU) around the US (2012 *National Statistics on Umbilical Vein Catheterizations.* 2012. *U.S. Department of Health and Human Services: Healthcare Cost and Utilization Project*. Accessed on 8 Jan. 2015, 2012 *National Statistics on Artery Catheterizations.* 2012. *U.S. Department of Health and Human Services: Healthcare Cost and Utilization Project*. Accessed on 8 Jan. 2015). The procedure is either performed immediately after the patient is brought into the ICU, or within a week of admission (because vessels remain patent for up to a week). A large number of these procedures are performed under emergency situations, particularly when resuscitation is required.

Before beginning the procedure, the patient is placed supine. The procedure involves grasping the umbilical cord, identifying the necessary vessel, dilating the vessel, introducing a flexible catheter, and guiding it to the appropriate location for the intervention. Imaging is then performed (usually x-ray) to confirm placement. There are a number of complications associated with this procedure, however, the biggest concern with this procedure is the low success rate, which ranges from 48% to 88% (R. Haase, M. Hein, V. Thale, C. Vilser, N. Merkel. 2011. *Umbilical Venous Catheters—Analysis of Malpositioning over a 10-Year Period. Z Geburtshilfe Neonatol,* 215 (1), 18-22, Vijay Gupta, Naresh Kumar, Atanu Kumar Jana, Niranjan Thomas. 2014. *A Modified Technique for Umbilical Arterial Catheterization. Indian Pediatrics,* 51 (8), 672). Introducing the catheter into the vessel is a major contributor to the low success rate. Further, the procedure requires 1-2 assistants to aid with cord retraction to introduce the catheter. These assistants would also need to be sufficiently sterilized for the procedure. Therefore there appears to be a need for a method to introduce a catheter into the umbilical cord without additional assistance, and with a higher rate of success. Improving the success rate of umbilical catheterizations will save lives, reduce treatment costs due to extended resource utilization, and minimize the occurrence of lengthened patient stay caused by complications.

SUMMARY OF INVENTION

The device is intended to allow a physician to prepare an umbilical cord by applying appropriate retraction and widening vessels (arteries and veins) to introduce the catheter. The device can be placed on the patient's abdomen, where it may or may not surround the umbilical cord. Once the device is placed, the umbilical cord can be retracted through a number of methods, all compatible with the device. This provides retraction as per the physician's requirements, without the need for any assistants. The device is indicated for use on neonates who require umbilical procedures, including but not limited to umbilical vascular catheterizations. The device is indicated for securing the umbilical cord during catheterization, and providing retraction. The device is also indicated for use in any facility where umbilical catheterizations are performed. The device is also indicated for use to retract other organs.

The device has two main components: a base and arms that are attached to the base. In some embodiments, the arms include a securing element that is attached to the umbilical cord. The tension in the securing element or arms can be adjusted to enable appropriate retraction. In some embodiments, the arms and base include an independent retraction device-securing element that can attach to an independent retraction device. This independent retraction device is then attached to the umbilical cord and enables appropriate retraction.

BRIEF DESCRIPTION OF THE DRAWINGS

The device and methods described herein are further described in terms of preferred embodiments. These preferred embodiments are described in detail with reference to the drawings. These embodiments are non-limiting preferred embodiments, in which like reference numerals represent similar structures throughout the several views of the drawings, and wherein:

FIG. 6A-B depict isometric views of bending arms of the third preferred embodiment of the present invention;

FIG. 8A-C depict isometric views of the fourth preferred embodiment of the present invention;

DETAILED DESCRIPTION OF THE INVENTION

Figure 1A:
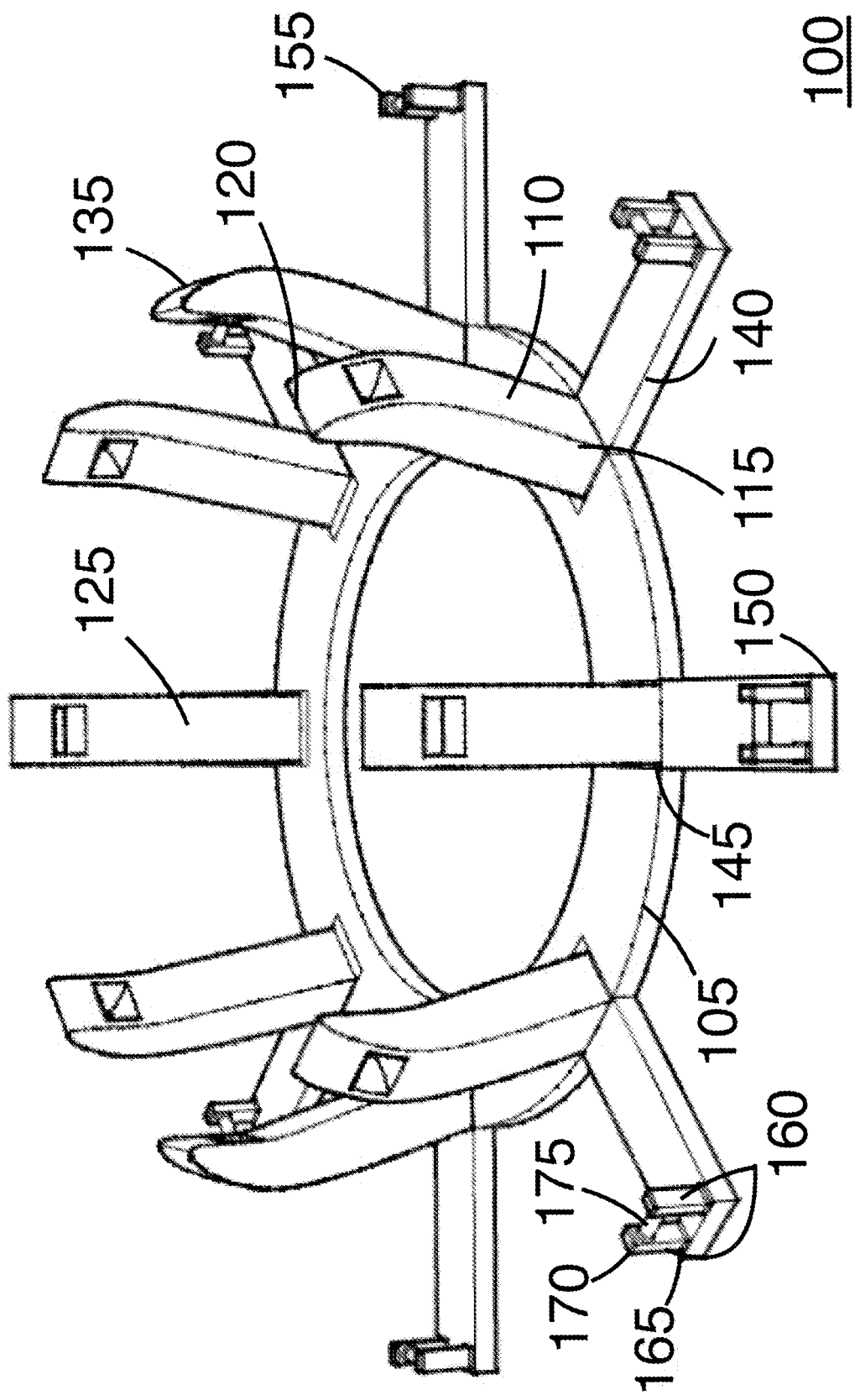
FIG. 1A-C depict isometric views of the first preferred embodiment of the present invention.

FIG. 1A is a general view of the first embodiment of the umbilical catheterization device 100. The umbilical catheterization device 100 includes a base 105 to which a plurality of vertical aims 110 is attached. The vertical aims 110 afford the physician a plurality of retraction angles. The vertical arms 110 each comprise a proximal end 115 and distal end 120, with the proximal end 115 connected to the base 105. The vertical arms 110 further comprise a proximal surface 125 and distal surface 130 (see FIG. 1C), bound by the proximal end 115 and distal end 120. The distal end 120 of the vertical arm 110 comprises the first independent retraction device-securing element 135. The first retraction independent device-securing element 135 is an opening that extends from the proximal surface 125 to distal surface 130 of the vertical aim 110.

The first embodiment of the umbilical catheterization device 100 further includes a plurality of horizontal arms 140 which are attached to the base 105. The horizontal arms 140 each comprise a proximal end 145 and distal end 150, with the proximal end 145 of the horizontal arm 140 attached to the base 105. The distal end 150 of the horizontal arm 140 comprises a second independent retraction device-securing element 155. The second independent retraction device-securing element 155 comprises two vertical columns 160, each with a proximal end 165 and distal end 170. The proximal end 165 of the vertical column 160 is attached to the distal end 150 of the horizontal arm 140. The second independent retraction device-securing element 155 further comprises a horizontal column 175, which is attached at either end to the vertical columns 160 at their distal ends 170.

Figure 1B:
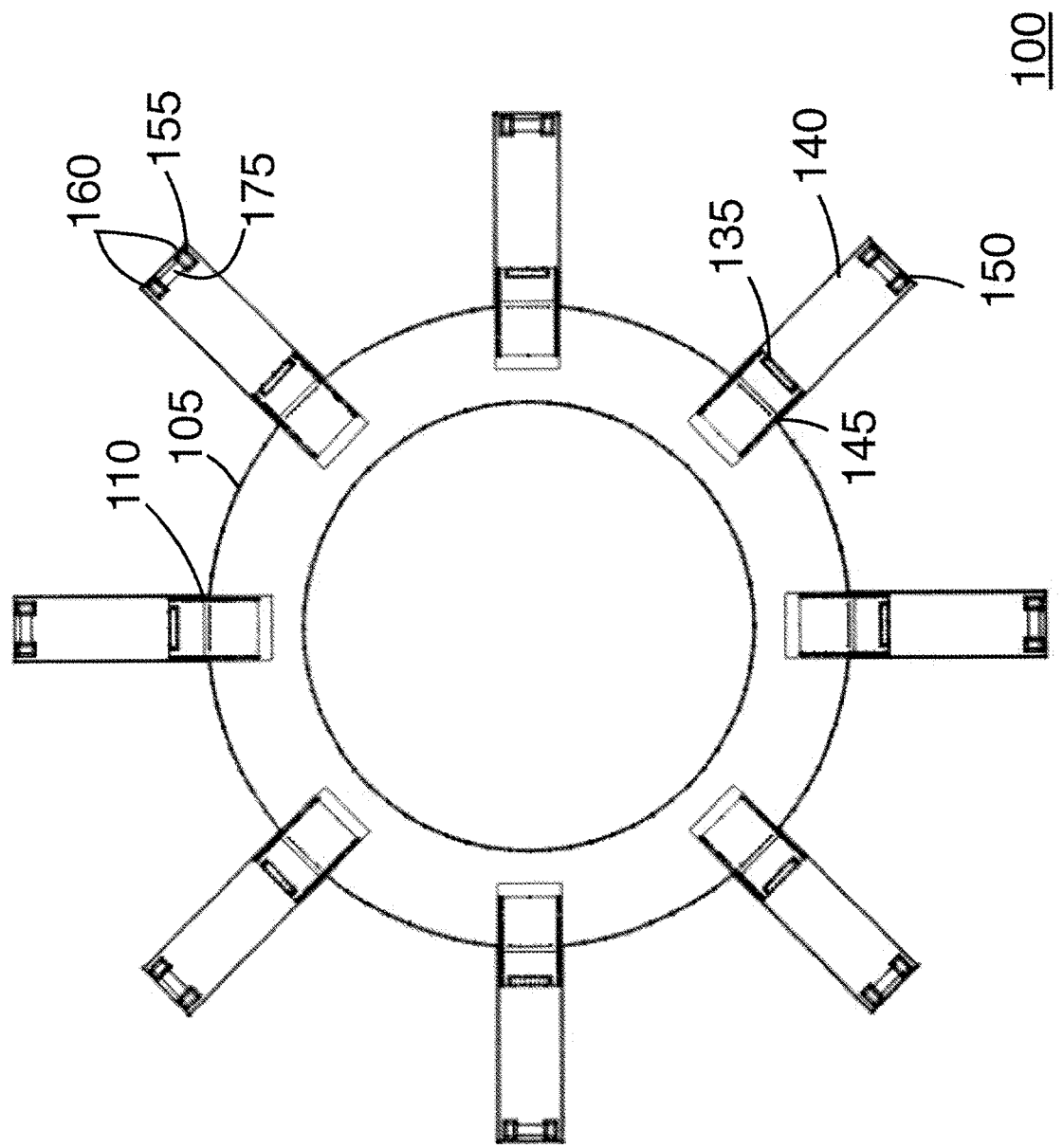
Figure 1C:
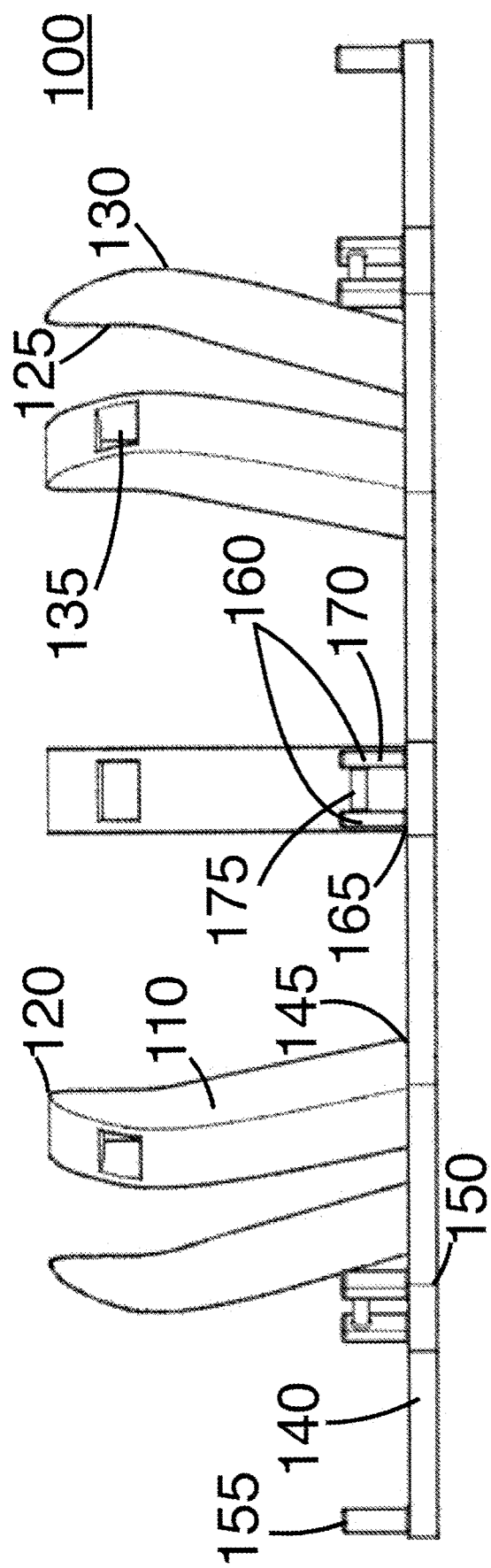

FIGS. 1B and 1C show alternate views of the first preferred embodiment of the umbilical catheterization device as described in FIG. 1.

Figure 2:
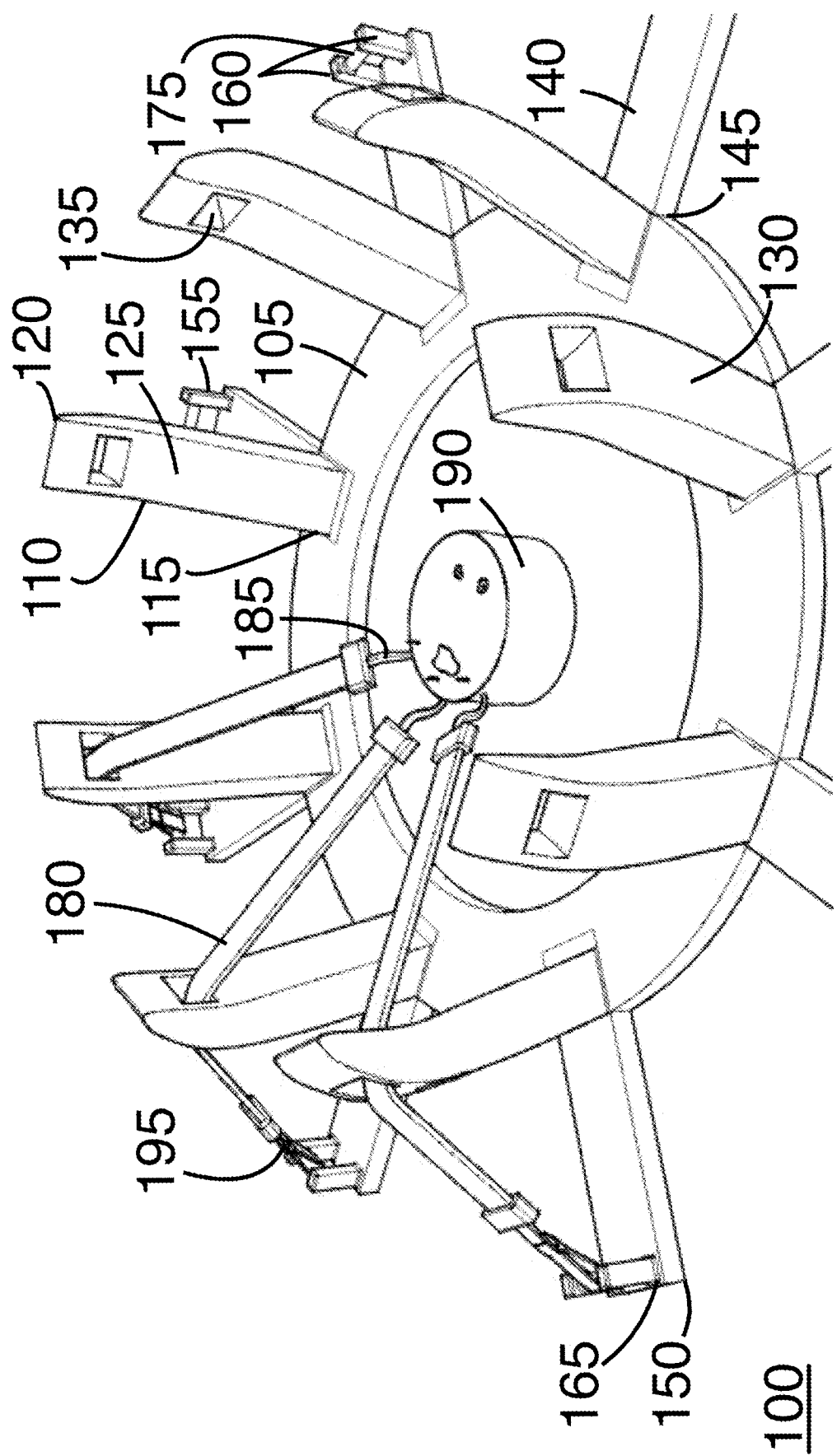
FIG. 2 depicts independent retraction devices working with the first preferred embodiment of the present invention.

FIG. 2 is a general view of the first embodiment of the umbilical catheterization device 100 as described in FIG. 1, working with an independent retraction device 180. A proximal end 185 of the independent retraction device 180 may attach to an umbilical cord 190, while a distal end 195 of the independent retraction device 180 may attach to the first independent retraction device-securing element 135. Alternatively, the distal end 195 of the independent retraction device 180 may pass through the first independent retraction device-securing element 135 and may attach to the second independent retraction device-securing element 155. The tension in the independent retraction device 180 may be adjusted to exert appropriate retraction on the umbilical cord 190.

The first independent retraction device-seeming element 135 enables the physician to attach an independent retraction device 180 that would aid in retracting the umbilical cord 190. The first independent retraction device-securing element 135 further enables the physician an to pass the independent retraction device 180 though the vertical aim 110 in order to attach the independent retraction device 180 to the second independent retraction device-securing element 155, thus increasing tension-induced retraction on the umbilical cord 190. The first embodiment of the umbilical catheterization device 100 may be constructed from a number of materials, which include, but are not limited to, polymers, metals, and composites. In some embodiments, the umbilical catheterization device 100 comprises a mechanism to attach the base 105 to the patient, or to drapes applied on top of the patient.

In some embodiments, the umbilical catheterization device 100 may be formed as one piece, for example, by injection molding, casting, or machining. In some embodiments, the umbilical catheterization device 100 may be formed by assembly of multiple parts, each formed by, for example, injection molding, casting, or machining. In some embodiments, the umbilical catheterization device 100 is a once used disposable device. In some embodiments, the umbilical catheterization device 100 may be sterilized and reused.

Figure 3A:
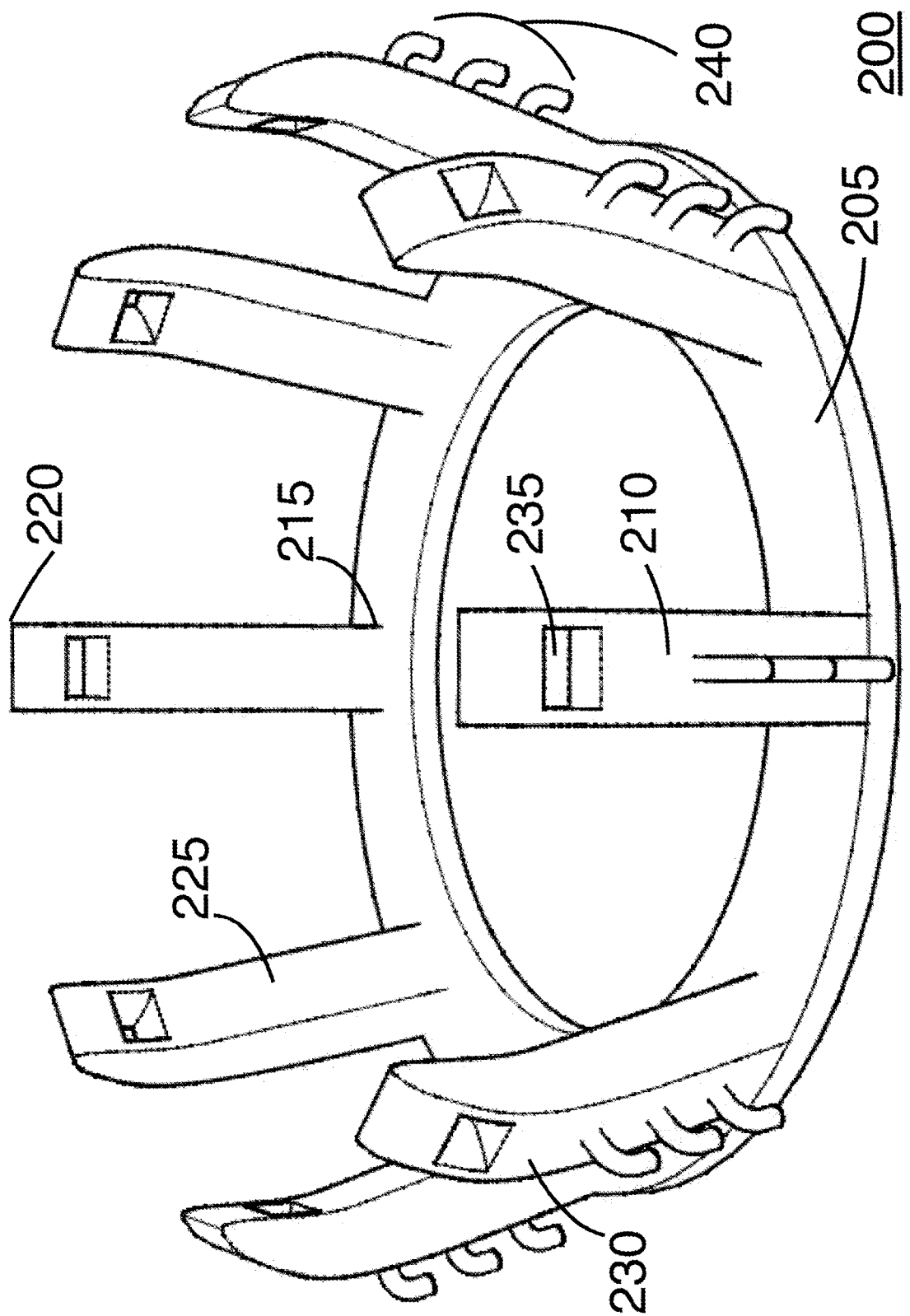
FIG. 3A-B depict isometric views of the second preferred embodiment of the present invention.

FIG. 3A is a general view of the second embodiment of the umbilical catheterization device 200. The umbilical catheterization device 200 includes a base 205 to which a plurality of vertical aims 210 is attached. The vertical aims 210 afford the physician a plurality of retraction angles. The vertical aims 210 each comprise a proximal end 215 and distal end 220, with the proximal end 215 connected to the base 205. The vertical arms 210 further comprise a proximal surface 225 and distal surface 230, bound by the proximal end 215 and distal end 220. The distal end 220 of the vertical aim 210 comprises the first independent retraction device-securing element 235. The first independent retraction device-securing element 235 is an opening that extends from the proximal surface 225 to distal surface 230 of the vertical aim 210.

The second embodiment of the umbilical catheterization device 200 further includes a second independent retraction device-seeming element 240. The second independent retraction device-securing element 240 is located on the distal surface 230 of the vertical arm 210. The second independent retraction device-securing element 240 comprises a plurality of downward curving members 245. The plurality of downward curving members 245 enable the physician to change the tension exerted.

Figure 3B:
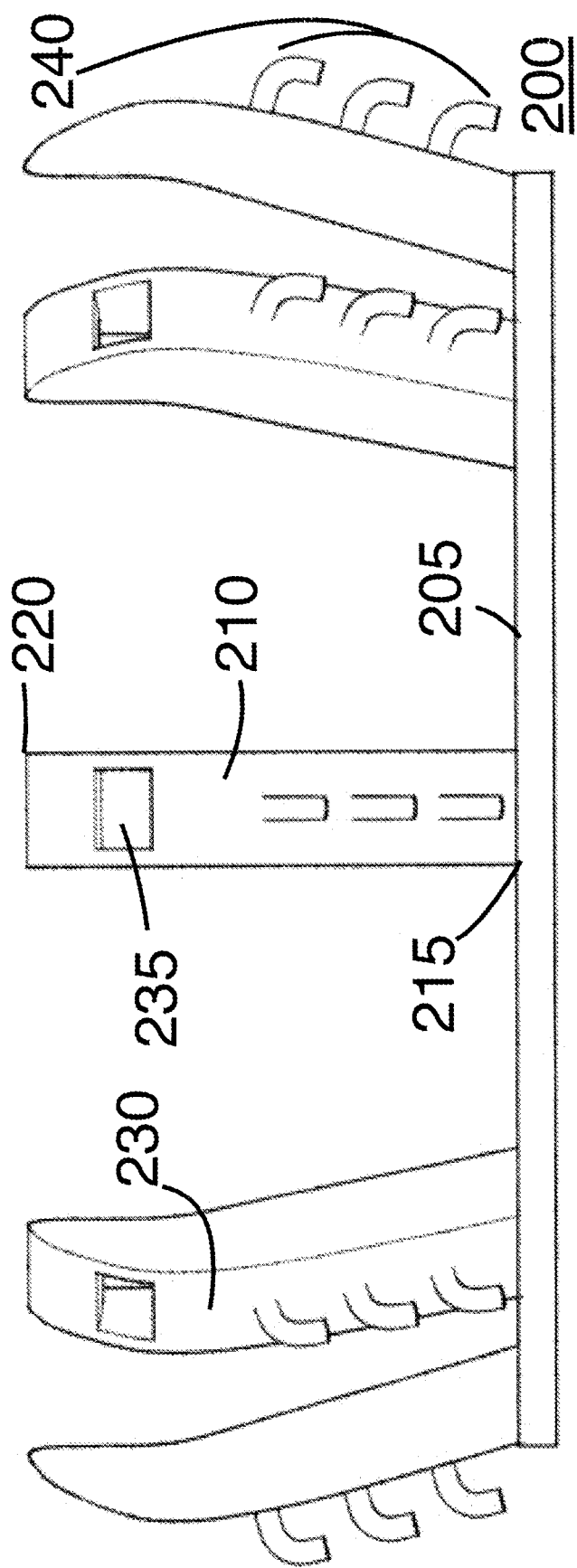

FIG. 3B shows an alternate view of the second preferred embodiment of the umbilical catheterization device 200 as described in FIG. 3A.

Figure 4:
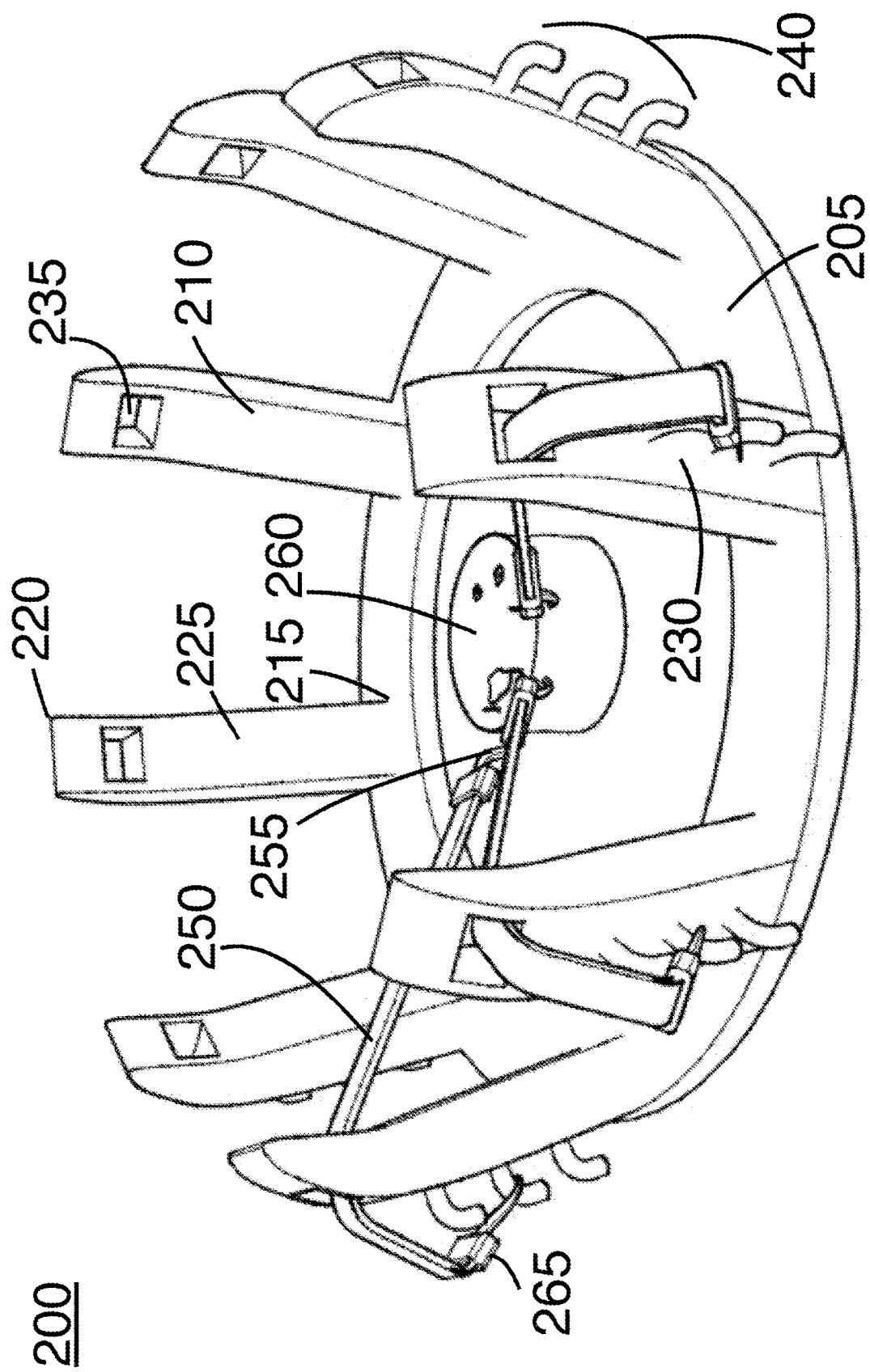
FIG. 4 depicts independent retraction devices working with the second preferred embodiment of the present invention.

FIG. 4 is a general view of the second embodiment of the umbilical catheterization device 200 as described in FIG. 3A, working with an independent retraction device 250. A proximal end 255 of the independent retraction device 250 may attach to an umbilical cord 260, while a distal end 265 of the independent retraction device 250 may attach to the first independent retraction device-securing element 235. Alternatively, the distal end 265 of the independent retraction device 250 may pass through the first independent retraction device-securing element 235 and may attach to the second independent retraction device-securing element 240. The tension in the independent retraction device 250 may be adjusted to exert appropriate retraction on the umbilical cord 260.

The first independent retraction device-securing element 235 enables the physician to attach an independent retraction device 250 that would aid in retracting the umbilical cord 260. The first independent retraction device-securing element 235 further enables the physician to pass the independent retraction device 250 though the vertical arm 210 in order to attach the independent retraction device 250 to the downward curving members 245, thus increasing tension-induced retraction on the umbilical cord 260. The second embodiment of the umbilical catheterization device 200 may be constructed from a number of materials, which include, but are not limited to, polymers, metals, and composites.

In some embodiments, the umbilical catheterization device 200 may be formed as one piece, for example, by injection molding, casting, or machining. In some embodiments, the umbilical catheterization device 200 may be formed by assembly of multiple parts, each formed by, for example, injection molding, casting, or machining. In some embodiments, the umbilical catheterization device 200 is a once used disposable device. In some embodiments, the umbilical catheterization device 200 may be sterilized and reused.

Figure 5:
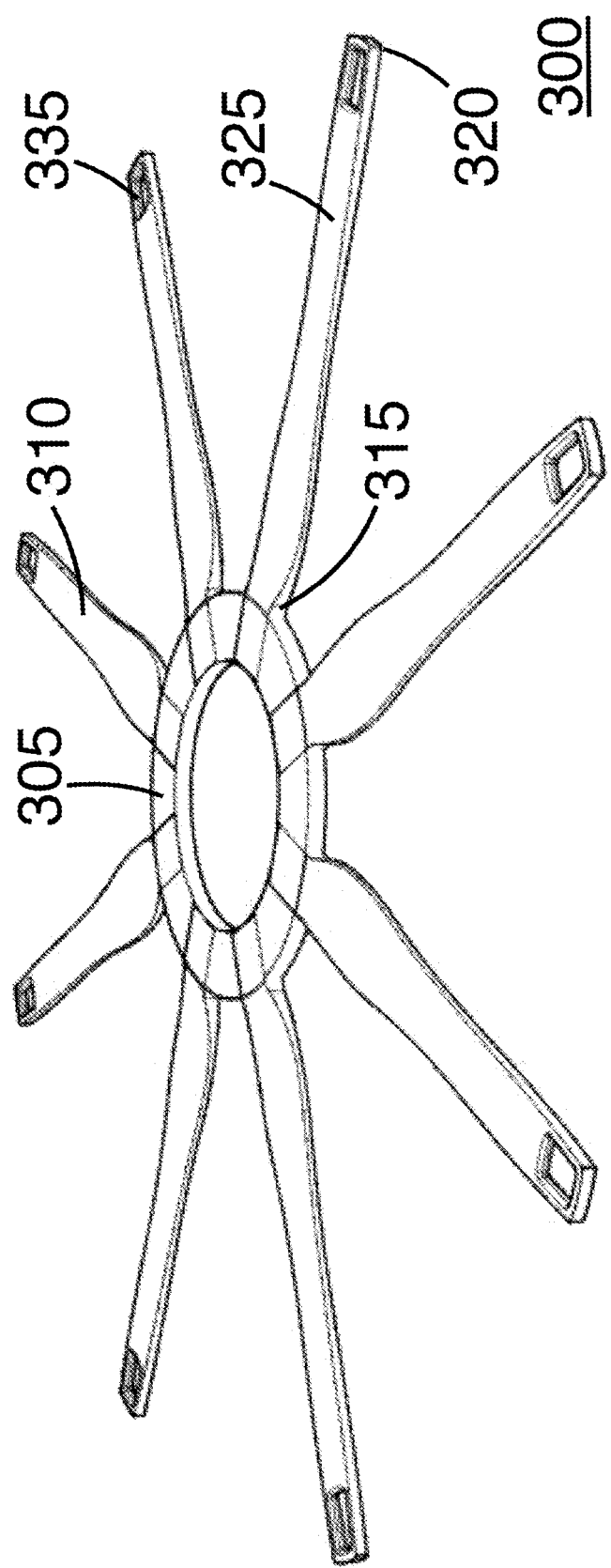
FIG. 5 depicts an isometric view of the third preferred embodiment of the present invention.

FIG. 5 is a general view of the third embodiment of the umbilical catheterization device 300. The umbilical catheterization device 300 includes a base 305 to which a plurality of arms 310 is attached. The aims 310 afford the physician a plurality of retraction angles. The arms 310 each comprise a proximal end 315 and distal end 320, with the proximal end 315 connected to the base 305. The arms 310 further comprise a proximal surface 325 and distal surface 330 (see FIG. 78), bound by the proximal end 315 and distal end 320. The distal end 330 of the arm 310 comprises an independent retraction device-securing element 335. The independent retraction device-securing element 335 is an opening that extends from the proximal surface 325 to distal surface 330 of the arm 310.

FIG. 6A-8 shows a general view of the third embodiment of the umbilical catheterization device 300 as described in FIG. 5, with the arms 310 bent such that the independent retraction device-securing element 335 is raised above the base 305 and at or above the distal end of the cut umbilical cord.

Figure 7A:
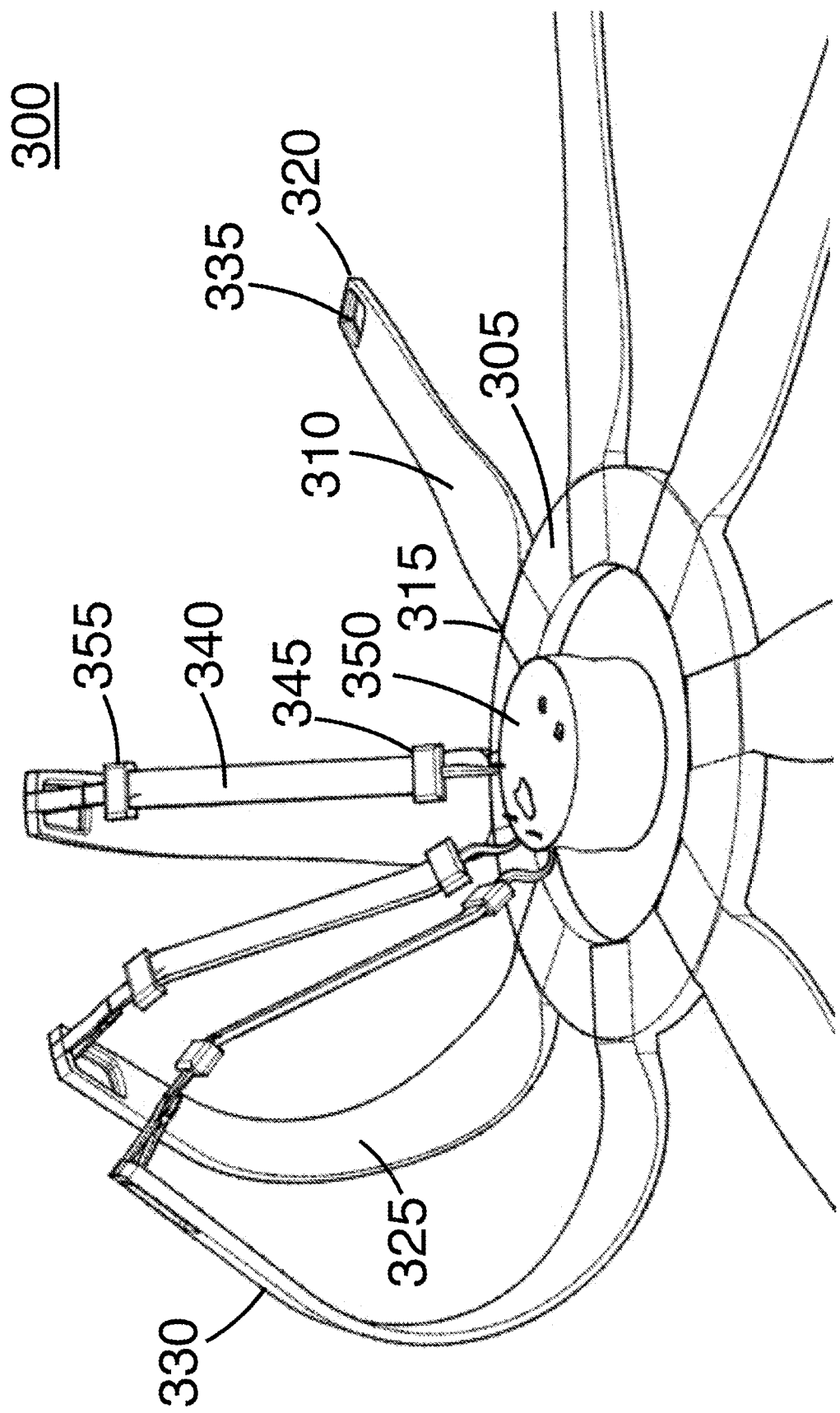
FIG. 7A-B depict independent retraction devices working with the third preferred embodiment of the present invention.
Figure 7B:
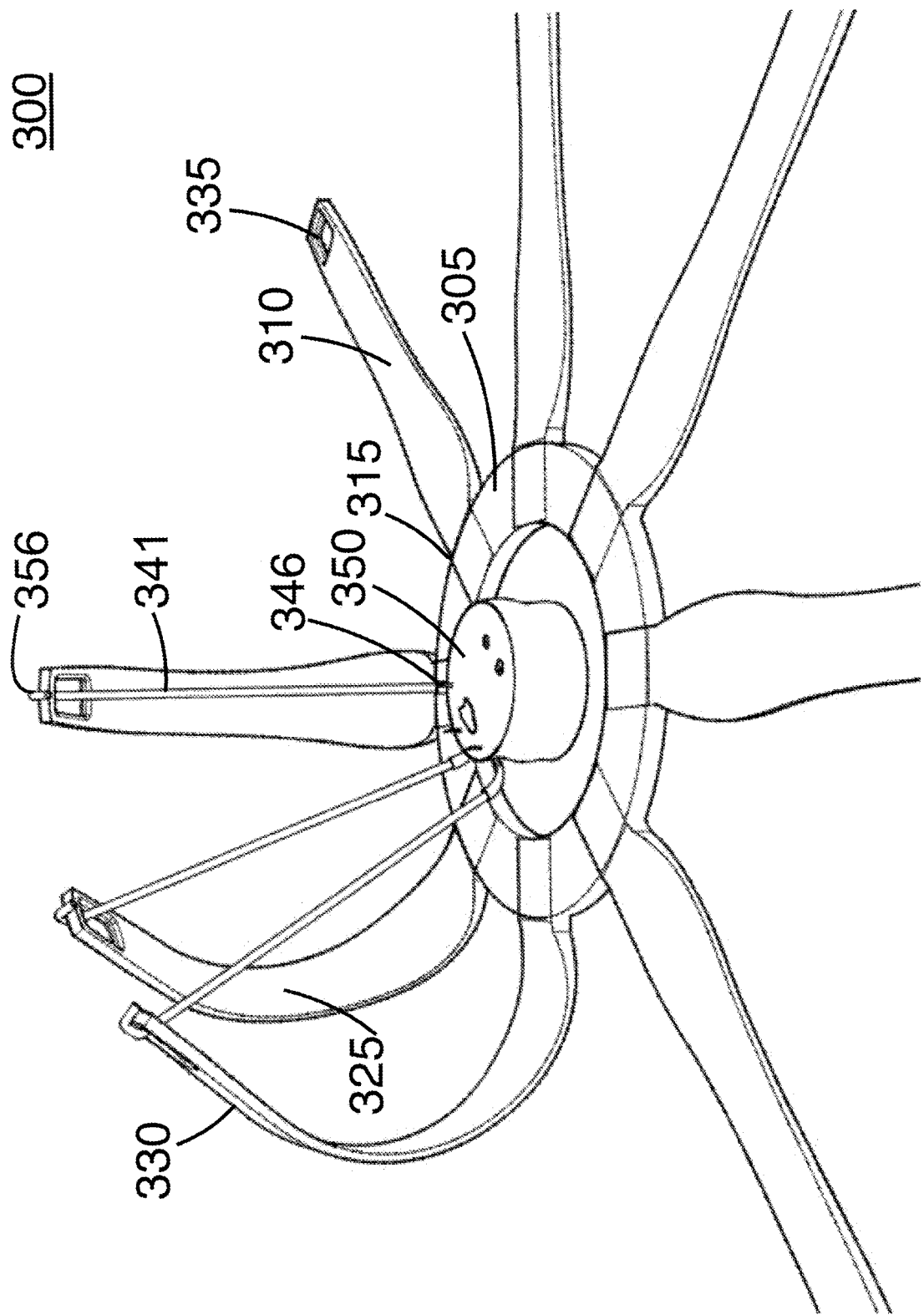

FIG. 7A is a general view of the third embodiment of the umbilical catheterization device 300 as described in FIG. 5, working with an independent retraction device 340. A proximal end 345 of the independent retraction device 340 may attach to an umbilical cord 350, while a distal end 355 of the independent retraction device 340 may attach to the independent retraction device-securing element 335. The arms 310 may be bent and/or adjusted to exert appropriate retraction on the umbilical cord 350.

FIG. 78 is a general view of the third embodiment of the umbilical catheterization device 300 as described in FIG. 5, working with another type of independent retraction device 341. A proximal end 346 of the independent retraction device 341 may attach to an umbilical cord 350, while a distal end 356 of the independent retraction device 341 may attach to the independent retraction device-securing element 335. The arms 310 may be bent and/or adjusted to exert appropriate retraction on the umbilical cord 350.

The independent retraction device-securing element 335 enables the physician to attach an independent retraction device 340 that would aid in retracting the umbilical cord 350. The arms 310 normally lay flat, but may be raised or bent to apply tension to retract the umbilical cord 350 as they attempt to return to normal position. The third embodiment of the umbilical catheterization device 300 may be constructed from a number of materials, which include, but are not limited to, polymers, metals, and composites.

In some embodiments, the umbilical catheterization device 300 may be formed as one piece, for example, by injection molding, casting, or machining. In some embodiments, the umbilical catheterization device 300 may be formed by assembly of multiple parts, each formed by, for example, injection molding, casting, or machining. In some embodiments, the umbilical catheterization device 300 is a once used disposable device. In some embodiments, the umbilical catheterization device 300 may be sterilized and reused.

Figure 8A:
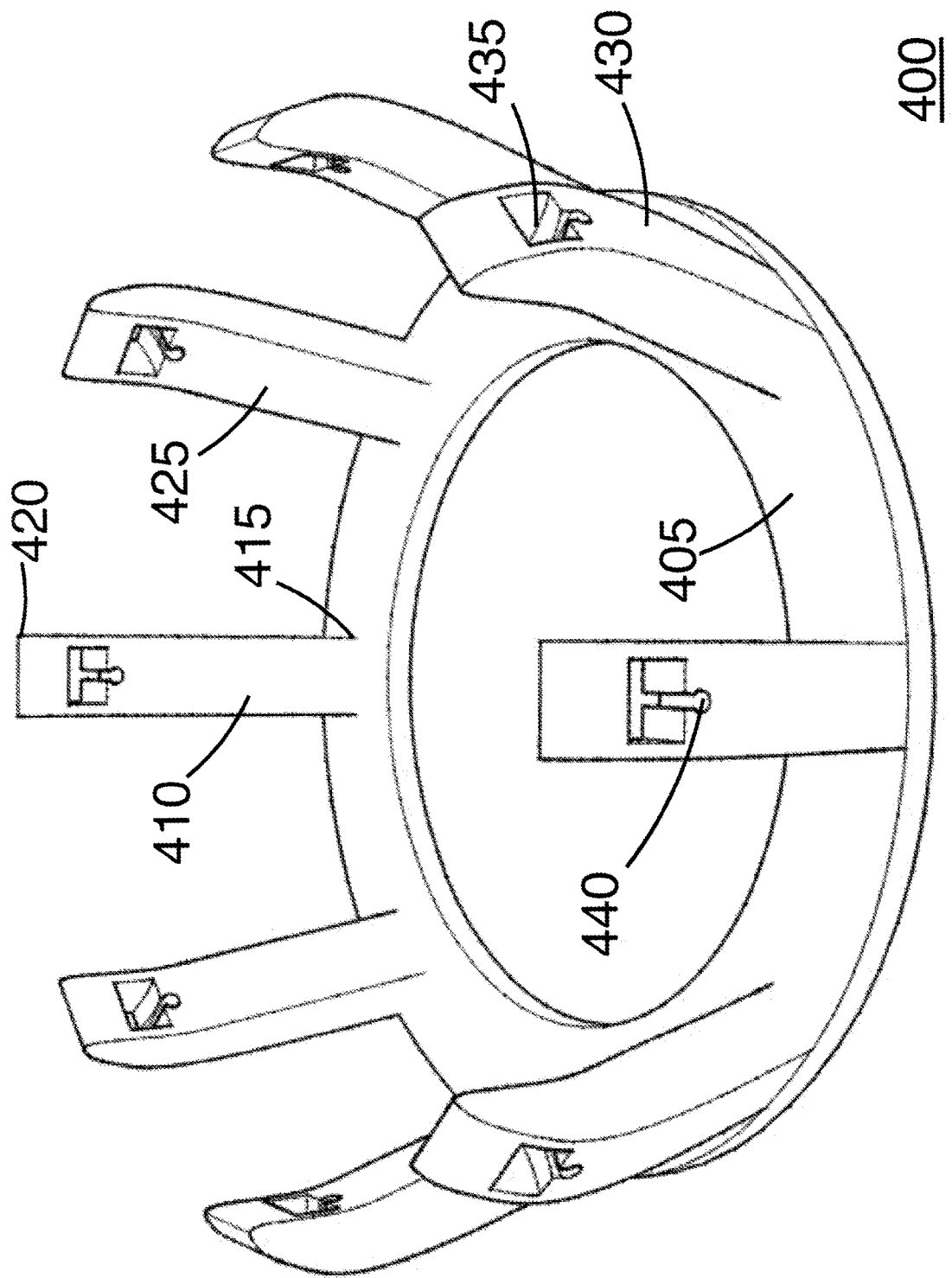

FIG. 8A is a general view of the fourth embodiment of the umbilical catheterization device 400. The umbilical catheterization device 400 includes a base 405 to which a plurality of vertical arms 410 is attached. The vertical arms 410 afford the physician a plurality of retraction angles. The vertical aims 410 each comprise a proximal end 415 and distal end 420, with the proximal end 415 connected to the base 405. The vertical arms 410 further comprise a proximal surface 425 and distal surface 430, bound by the proximal end 415 and distal end 420. The distal end 420 of the vertical aim 410 comprises the first independent retraction device-securing element 435. The first independent retraction device-securing element 435 is an opening that extends from the proximal surface 425 to distal surface 430 of the vertical aim 410.

The fourth embodiment of the umbilical catheterization device 400 further includes a second independent retraction device-securing element 440. The second independent retraction device-securing element 440 comprises a shaft extending from the proximal surface 425 to distal surface 430 of a vertical aim 410, with an opening towards the first independent retraction device-securing element 435.

Figure 8C:
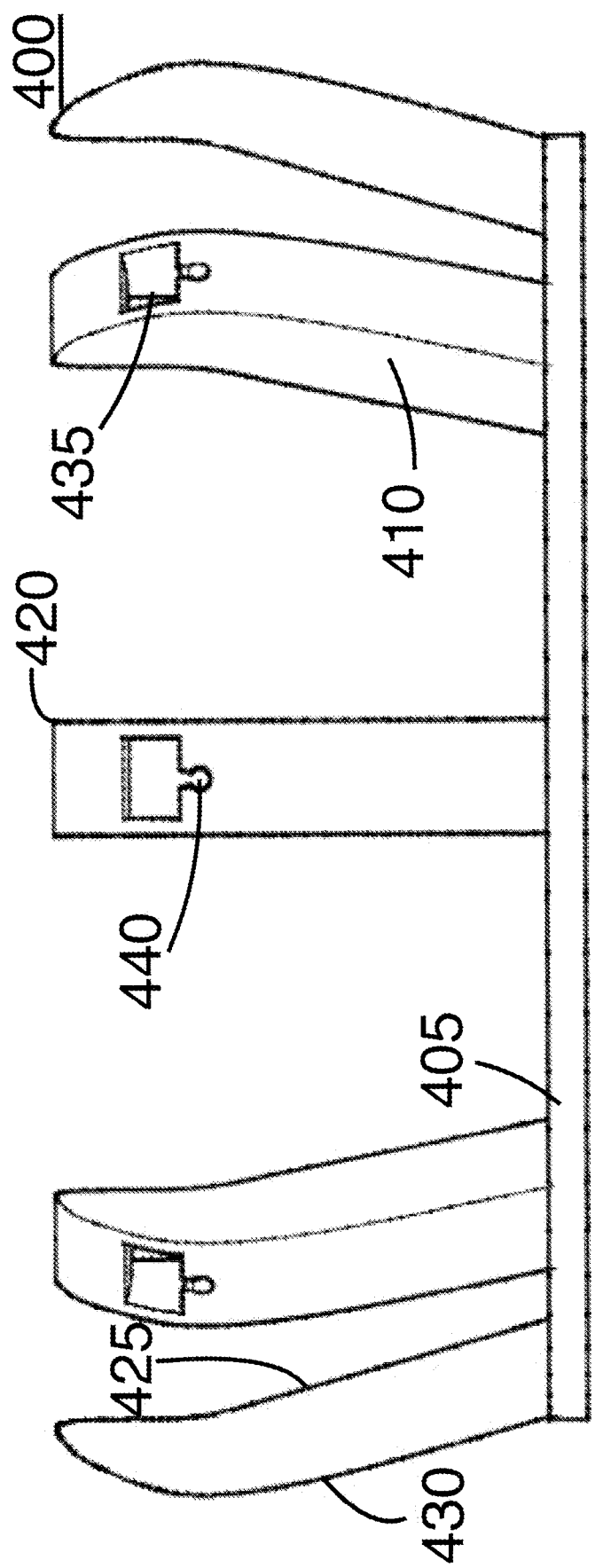

FIG. 8B-C show alternate views of the fourth preferred embodiment of the umbilical catheterization device 400 as described in FIG. 8A.

Figure 9:
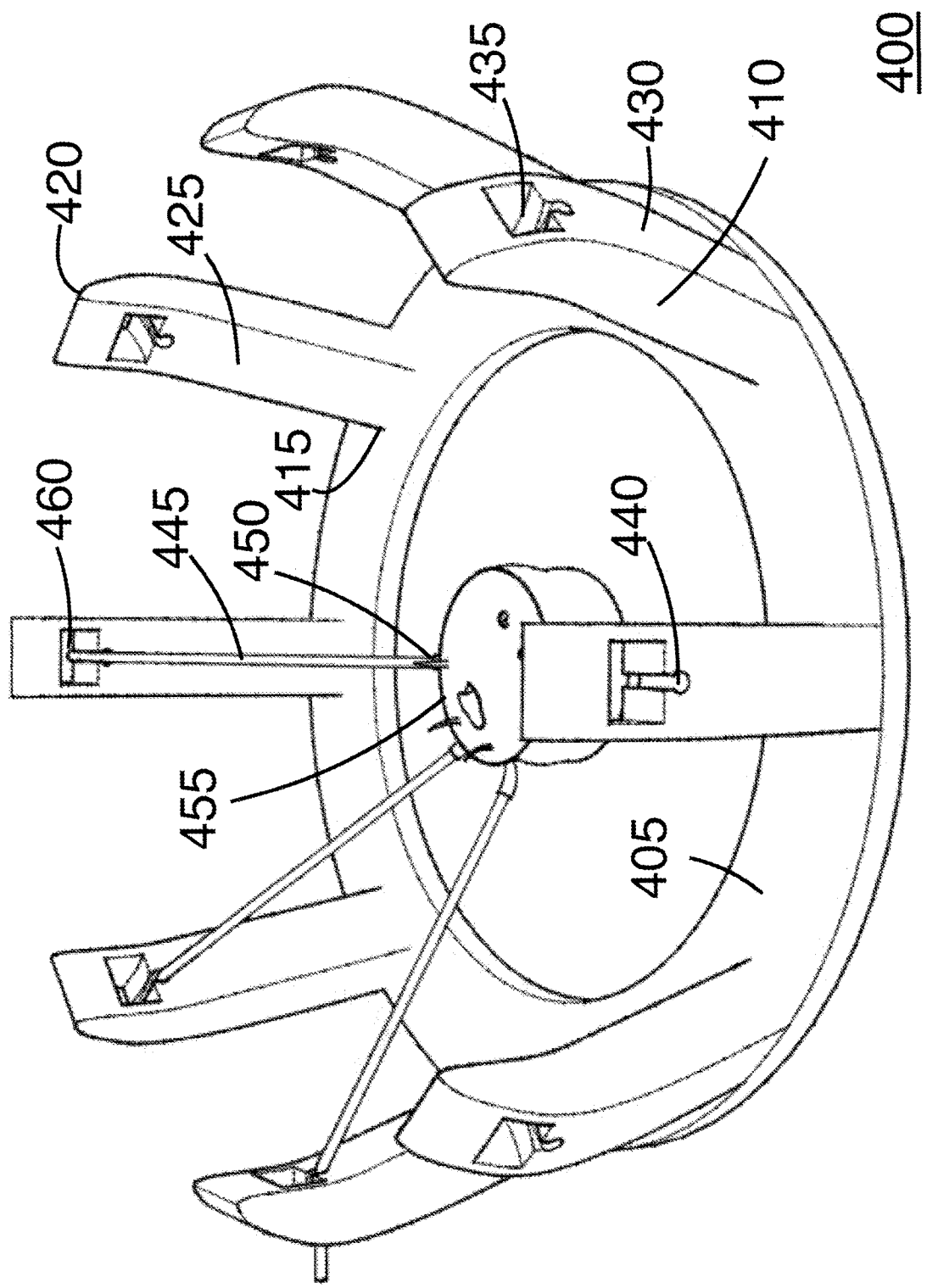
FIG. 9 depicts independent retraction devices working with the fourth preferred embodiment of the present invention.

FIG. 9 is a general view of the fourth embodiment of the umbilical catheterization device 400 as described in FIG. 8A, working with an independent retraction device 445. The proximal end 450 of the independent retraction device 445 may attach to the umbilical cord 455, while the distal end 460 of the independent retraction device 445 may attach to the first independent retraction device-securing element 435. Alternatively, the distal end 460 of the independent retraction device 445 may pass through the first independent retraction device-securing element 435 and may be pulled down and secured within the second independent retraction device-securing element 440. The tension in the independent retraction device 445 may be adjusted to exert appropriate retraction on the umbilical cord 455.

The first retraction device-securing element 435 enables the physician to secure an independent retraction device 445 that would aid in retracting the umbilical cord 455. The first independent retraction device-securing element 435 further enables the physician to pass the independent retraction device 445 though the vertical arm 410 in order to pull down and secure the independent retraction device 445 within the second independent retraction device-securing element 440, thus increasing tension-induced retraction on the umbilical cord 455. The fourth embodiment of the umbilical catheterization device 400 may be constructed from a number of materials, which include, but are not limited to, polymers, metals, and composites.

In some embodiments, the umbilical catheterization device 400 may be formed as one piece, for example, by injection molding, casting, or machining. In some embodiments, the umbilical catheterization device 400 may be formed by assembly of multiple parts, each formed by, for example, injection molding, casting, or machining. In some embodiments, the umbilical catheterization device 400 is a once used disposable device. In some embodiments, the umbilical catheterization device 400 may be sterilized and reused.

Figure 10:
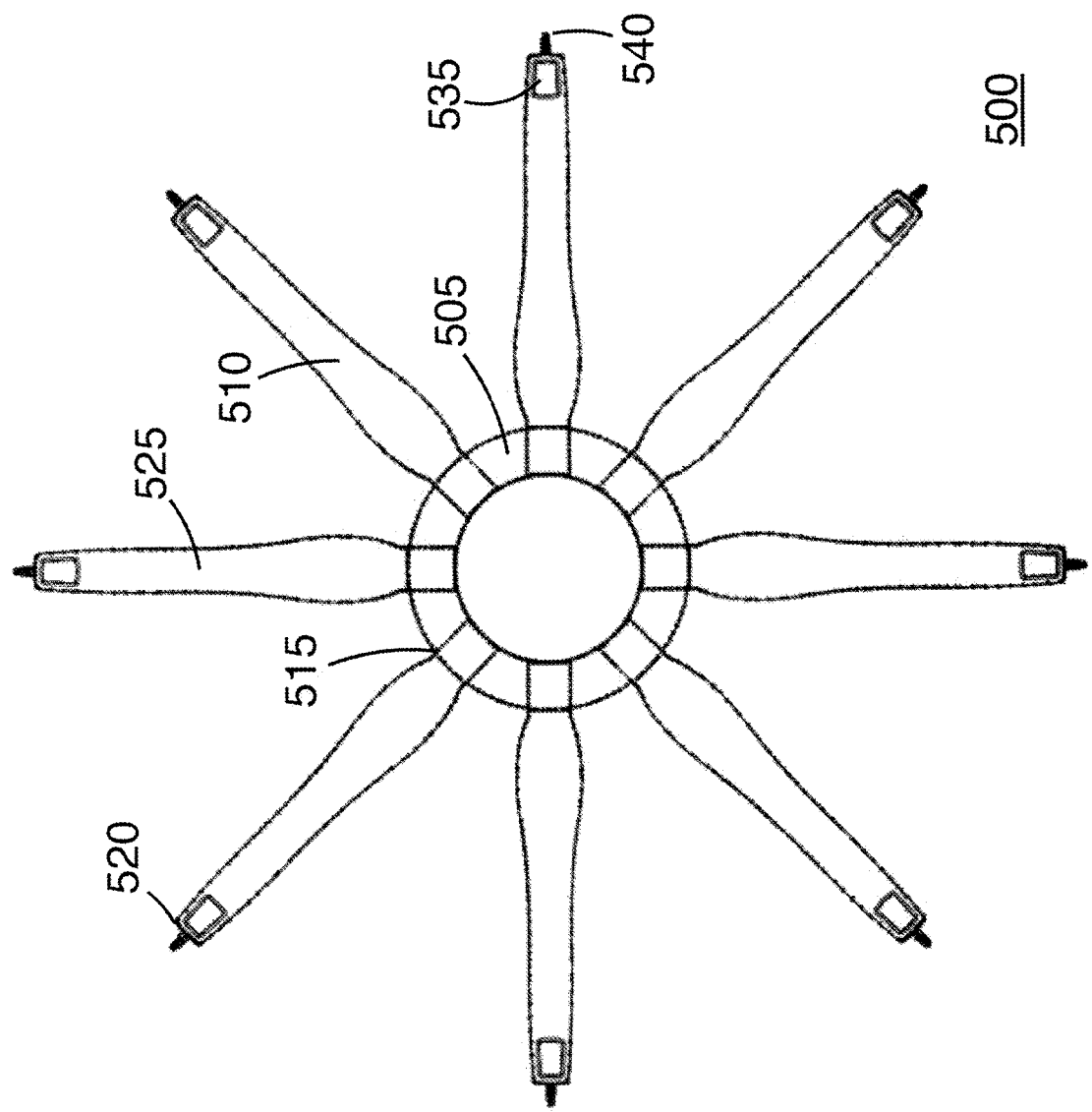
FIG. 10 depicts the fifth preferred embodiment of the present invention.

FIG. 10 is a general view of the fifth embodiment of the umbilical catheterization device 500. The fifth embodiment of the umbilical catheterization device 500 includes a base 505 to which a plurality of arms 510 is attached. The arms 510 afford the physician a plurality of retraction angles. The arms 510 each comprise a proximal end 515 and distal end 520, with the proximal end 515 connected to the base 505. The arms 510 further comprise a proximal surface 525 and distal surface 530, bound by the proximal end 515 and distal end 520. The distal end 520 of the arm 510 comprises an independent retraction device-securing element 535. The independent retraction device-securing element 535 is an opening that extends from the proximal surface 525 to distal surface 530 (see FIG. 11) of the arm 510.

The fifth embodiment of the umbilical catheterization device 500 further includes a cut umbilical cord-securing element 540. The cut umbilical cord-securing element 540 comprises an integrated securement element, such as a hook 545 with a proximal end 550 (see FIG. 11) and distal end 555 (see FIG. 11). The proximal end 550 of the hook 545 is attached to the distal end 520 of the aim 510.

Figure 11:
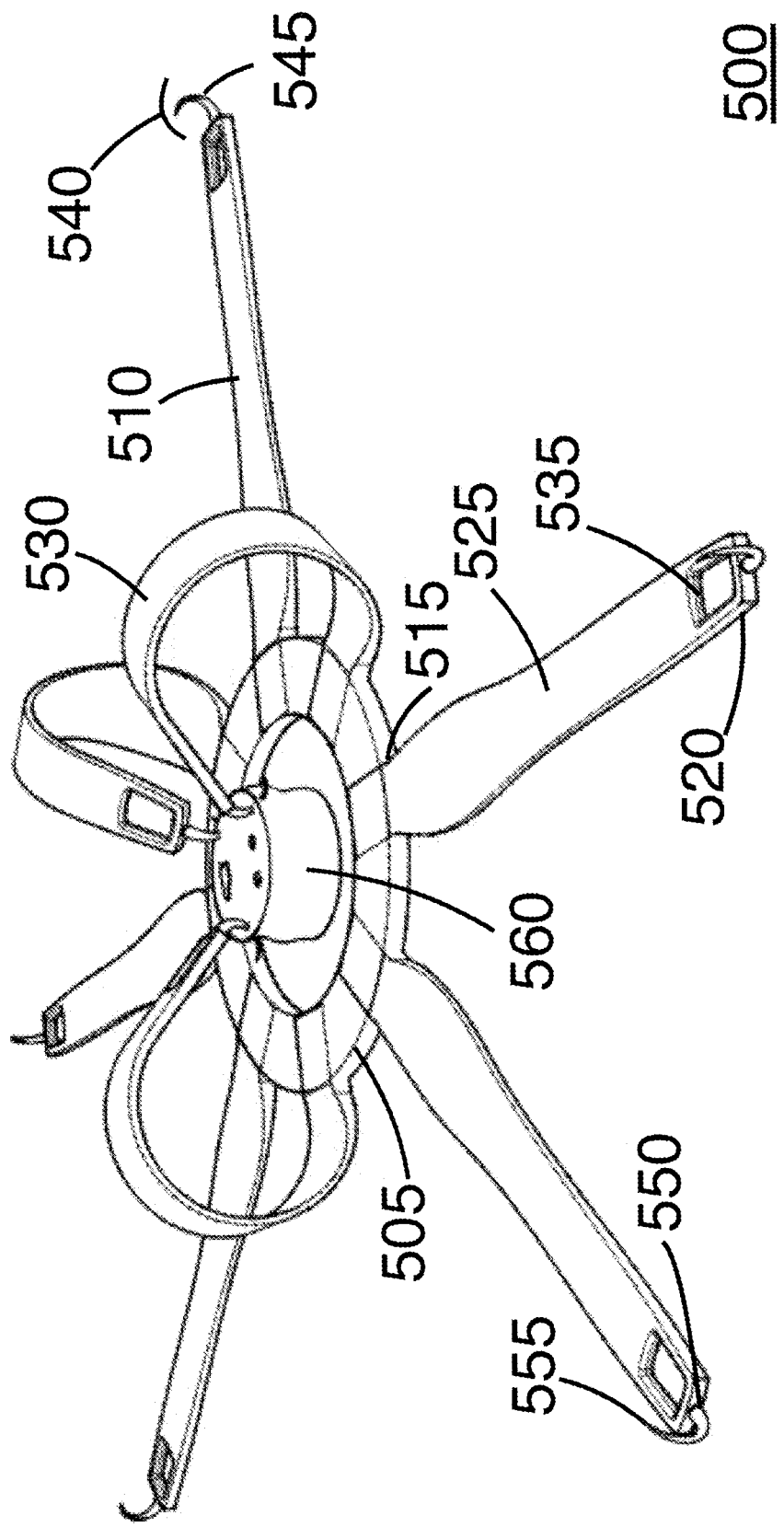
FIG. 11 depicts the fifth preferred embodiment of the present invention retracting the umbilical cord.

FIG. 11 is a general view of the fifth embodiment of the umbilical catheterization device 500 as described in FIG. 10. The aims 510 may be bent and/or adjusted such that the cut umbilical cord-securing element 540 is attached to the umbilical cord 560, thus directly aiding in retraction of the umbilical cord 560.

The independent retraction device-securing element 535 enables the physician to attach an independent retraction device that would aid in retracting the umbilical cord 560. The arms 510 may be raised or bent to apply tension to retract the umbilical cord 560. Alternatively, the cut umbilical cord-securing element 540 may be attached to the umbilical cord 560 directly to enable retraction. The aims 510 normally lay flat, but may be raised or bent to apply tension to retract the umbilical cord 560. The fifth embodiment of the umbilical catheterization device 500 may be constructed from a number of materials, which include, but are not limited to, polymers, metals, and composites.

In some embodiments, the umbilical catheterization device 500 may be formed as one piece, for example, by injection molding, casting, or machining. In some embodiments, the umbilical catheterization device 500 may be formed by assembly of multiple parts, each formed by, for example, injection molding, casting, or machining. In some embodiments, the umbilical catheterization device 500 is a once used disposable device. In some embodiments, the umbilical catheterization device 500 may be sterilized and reused.

METHOD OF OPERATION—The first embodiment of the umbilical catheterization device 100 may be used with other instruments currently employed to perform umbilical catheterizations. Prior to use, the patient is placed supine, and is appropriately sterilized. The umbilical cord 190 is cleaned, and appropriately prepared. Once the umbilical cord 190 has been prepared, the first embodiment of the umbilical catheterization device 100 is placed around the umbilical cord 190, such that the umbilical cord 190 passes through the base 105 of the first embodiment of the umbilical catheterization device 100. The first embodiment of the umbilical catheterization device 100 may adhere to the patient's skin through adhesives on the base 105, or may be clamped to the cloth drapes placed around the umbilical cord 190 using standard surgical clamps. The first embodiment of the umbilical catheterization device 100 may also be secured to the patient's body through other means. The umbilical cord 190 should be cut at the required angle and height from abdomen, but this height should not exceed 2 cm, per current procedural guidelines. After bleeding has been controlled, the physician may choose the type of independent retraction device 180. In the first embodiment of the umbilical catheterization device 100, the proximal end 185 of the independent retraction device 180 may first be attached to the upper edge of the umbilical cord 190. The distal end 195 of the independent retraction device 180 may then pass through the first independent retraction device-securing element 135, and then may attach to the second independent retraction device-securing element 155. Tension in the independent retraction device 180 may be altered as appropriate to induce required retraction on the umbilical cord 190. Once the umbilical cord 190 has been held in place and retracted the required length and angle, the rest of the procedures involved in umbilical catheterization may be performed.

The second embodiment of the umbilical catheterization device 200 has a similar method of operation as the first embodiment of the umbilical catheterization device 100. After the proximal end 255 of the independent retraction device 250 is attached to the upper edge of the umbilical cord 260, the distal end 265 of the independent retraction device 250 may then pass through the first independent retraction device-securing element 235. The distal end 265 of the independent retraction device 250 may then attach to the downward curving members 245 on the second independent retraction device-securing element 240. Tension in the independent retraction device 250 may be altered as appropriate to induce required retraction on the umbilical cord 260, by, for example, selecting an appropriate one of the downward curving members 245.

The third embodiment of the umbilical catheterization device 300 has a similar method of operation as the first embodiment of the umbilical catheterization device 100. Referring to FIG. 7A and FIG. 78, after the proximal end 345 or 346 of the independent retraction device 340 or 341 is attached to the upper edge of the umbilical cord 350, the distal end 355 or 356 of the independent retraction device 340 or 341 may then attach to the independent retraction device-securing element 335. The arms 310 may be bent and/or adjusted to exert appropriate retraction on the umbilical cord 350.

The fourth embodiment of the umbilical catheterization device 400 has a similar method of operation as the first embodiment of the umbilical catheterization device 100. After the proximal end 450 of the independent retraction device 445 is attached to the upper edge of the umbilical cord 455, the distal end 460 of the independent retraction device 445 may then pass through the first independent retraction device-securing element 435. The distal end 460 of the independent retraction device 445 may then be pulled downward to be secured within the second independent retraction device-securing element 440. Tension in the independent retraction device 445 may be altered as appropriate to induce required retraction on the umbilical cord 455.

The fifth embodiment of the umbilical catheterization device 500 has the same method of operation as the first embodiment of the umbilical catheterization device 100, with some modifications. After the umbilical cord 560 has been cut and prepared, the arm 510 may be bent and/or adjusted such that the cut umbilical cord-securing element 540 is attached to the umbilical cord 560.

The invention claimed is:
1. A method of retracting an umbilical cord, comprising:
providing an umbilical cord retraction device including a support base with an upper surface and lower surface, one or more arms attached to the support base, each of the one or more arms including a proximal end attached to the base and a free distal end, and one or more attaching elements disposed at the free distal end of each of the one or more arms;
placing the support base of the umbilical cord retraction device proximate to an abdominal surface of a subject, such that the support base at least partially surrounds an area large enough to allow passage of an umbilical cord of the subject;
accessing the umbilical cord of the subject in the surrounded area;
bending the one or more arms from an original shape toward a center of the support base;

securing the free distal end of each of the one or more arms to a cut end of the umbilical cord via the one or more attaching elements; and allowing the one or more arms to flex back toward the original shape, thereby providing retraction of the umbilical cord at least partially upward from the abdominal surface.

2. The method of claim 1, wherein the allowing the one or more arms to flex back toward the original shape further provides radial retraction of the cut end of the umbilical cord away from the center of the support base.

3. The method of claim 1, wherein the securing the free distal ends of the one or more arms to the cut end of the umbilical cord includes securing a plurality of the one or more arms to different locations around a perimeter of the cut end of the umbilical cord.

4. The method of claim 1, wherein the lower surface of the support base is substantially flat, and the placing the support base of the umbilical cord retraction device proximate to the abdominal surface of the subject includes resting the substantially flat lower surface of the support base on the abdominal surface of the subject.

5. An umbilical cord retraction device, comprising:
a base with an upper surface and lower surface, the lower surface being configured to be stabilized at rest on an abdominal surface that at least partially surrounds an area, the area being large enough to allow passage of an umbilical cord;
one or more arms attached to the base, each of the one or more arms including a proximal end attached to the base and a free distal end opposite the proximal end;
a securing element disposed at least one of on or through at least one of an anterior surface of the one or more arms or a portion of the base that extends outward from an attachment point of the one or more arms and the base; and
an independent retraction device including a first end configured to attach to a cut end of an umbilical cord, and a second end, opposite the first end, configured to attach to the securing element,
wherein:
the umbilical cord retraction device is configured to retract, through a hole in the base, an umbilical cord at least partially upward from the abdominal surface via securing the first end of the independent retraction device to a cut end of an umbilical cord, and securing the second end of the independent retraction device to the securing element,
the independent retraction device is configured to be at least one of routed through an opening in the free distal end of the one or more arms, or attached to the free distal end of the one or more arms, during the retraction of the umbilical cord, and
each of the one or more arms extend at least partially outward from the base and is configured to assist with retraction of the umbilical cord by bending each of the one or more arms from an original shape toward a center of the base, securing the independent retraction device to the cut end of the umbilical cord and the securing element, and allowing the one or more arms to flex back toward the original shape.

6. The umbilical cord retraction device of claim 5, wherein the umbilical cord retraction device is further configured such that the allowing the one or more arms to flex back toward the original shape provides radial retraction of the cut end of the umbilical cord in a plurality of opposing directions.

7. The umbilical cord retraction device of claim 5, wherein the umbilical cord retraction device is configured to be at least partially secured in position during umbilical cord retraction via a combination of the independent retraction device exerting tension to provide retraction of the umbilical cord, and the lower surface of the base is configured to exert a downward force on the abdominal surface to counter the tension exerted by the independent retraction device.

8. The umbilical cord retraction device of claim 5, wherein the free distal end of at least one of the one or more arms is formed to extend at or above the retracted cut end of the umbilical cord while the lower surface of the base rests on the abdominal surface.

9. The umbilical cord retraction device of claim 5, wherein the base is formed to lie in a base plane, the one or more arms lie in the base plane in the original shape, and the one or more arms are configured to be bent out of the base plane and to provide the retraction of the umbilical cord via the one or more arms flexing back toward the original shape.

10. The umbilical cord retraction device of claim 5, wherein the umbilical cord retraction device includes a plurality of the one or more arms disposed at different locations around the base, each of the plurality of arms including one or more of the securing elements.

11. The umbilical cord retraction device of claim 5, wherein the base is flat and includes a central void through which the umbilical cord is retracted.

12. The umbilical cord retraction device of claim 5, wherein the one or more arms are formed of a polymer material.

13. The umbilical cord retraction device of claim 5, wherein the base is formed of a polymer material.

14. An umbilical cord retraction device, comprising:
a base with an upper surface and lower surface, the lower surface being configured to be stabilized at rest on an abdominal surface that at least partially surrounds an area, the area being large enough to allow passage of an umbilical cord;
one or more arms attached to the base, each of the one or more arms including a proximal end attached to the base and a free distal end opposite the proximal end;
a securing element disposed at least one of on or through at least one of an anterior surface of the one or more arms or a portion of the base that extends outward from an attachment point of the one or more arms and the base; and
an independent retraction device including a first end configured to attach to a cut end of an umbilical cord, and a second end, opposite the first end, configured to attach to the securing element,
wherein:
the umbilical cord retraction device is configured to retract, through a hole in the base, an umbilical cord at least partially upward from the abdominal surface via securing the first end of the independent retraction device to a cut end of an umbilical cord, and securing the second end of the independent retraction device to the securing element,
the independent retraction device is configured to be at least one of routed through an opening in the free distal end of the one or more arms, or attached to the free distal end of the one or more arms, during the retraction of the umbilical cord, and
the umbilical cord retraction device includes a plurality of the securing elements for each of the one or more arms, the plurality of securing elements disposed at different locations along the at least one of anterior surface of the one or more arms or portion of the base, such that an effective length of the independent retraction device is adjusted by securing the independent retraction device to different securing elements.

15. The umbilical cord retraction device of claim 14, wherein the umbilical cord retraction device is further configured such that the securing the first end of the independent retraction device to the cut end of the umbilical cord, and the securing the second end of the independent retraction device to the securing element provide radial retraction of the cut end of the umbilical cord in a plurality of opposing directions.

16. The umbilical cord retraction device of claim 14, wherein the securing element includes at least one of a plurality of voids and a plurality of extending members configured to enable the adjusting of a tension applied by the independent retraction device to the umbilical cord by securing the independent retraction device to different locations on the one or more arms or base.

17. The umbilical cord retraction device of claim 14, wherein the umbilical cord retraction device is further configured to be at least partially secured in position during umbilical cord retraction via a combination of the one or more arms exerting a tension to provide the retraction of the umbilical cord, and the lower surface of the base is configured to exert a downward force on the abdominal surface to counter the tension exerted by the one or more arms.

18. The umbilical cord retraction device of claim 14, wherein the one or more arms are formed of a polymer material.

19. The umbilical cord retraction device of claim 14, wherein the base is formed of a polymer material.

* * * * *